United States Patent [19]

Engel et al.

[11] Patent Number: 6,080,543
[45] Date of Patent: Jun. 27, 2000

[54] DETECTION OF FUNGAL PATHOGENS

[75] Inventors: Stacia R. Engel; Richard A. Descenzo; Nancy A. Irelan, all of Modesto, Calif.

[73] Assignee: E. & J. Gallo Winery, Modesto, Calif.

[21] Appl. No.: 08/986,727

[22] Filed: Dec. 8, 1997

[51] Int. Cl.$^7$ .............................. C12Q 1/68; C07H 21/04; C12P 19/34

[52] U.S. Cl. ............................ 435/6; 435/91.2; 435/810; 536/23.1; 536/24.32; 536/24.33

[58] Field of Search .............................. 435/6, 91.2, 810; 536/24.32, 24.33, 23.1

[56] References Cited

U.S. PATENT DOCUMENTS

| | | | |
|---|---|---|---|
| 4,230,625 | 10/1980 | Despreaux et al. | 260/397.1 |
| 4,301,246 | 11/1981 | Despreaux et al. | 435/58 |
| 5,149,624 | 9/1992 | Gabriel | 435/6 |
| 5,389,513 | 2/1995 | Baquero et al. | 435/6 |
| 5,389,515 | 2/1995 | Chmelo et al. | 435/6 |
| 5,403,710 | 4/1995 | Weisburg et al. | 435/6 |
| 5,426,027 | 6/1995 | Lott et al. | 435/6 |
| 5,434,048 | 7/1995 | Simon et al. | 435/6 |
| 5,545,525 | 8/1996 | Montplaisir et al. | 435/6 |
| 5,580,971 | 12/1996 | Mitsuhashi | 536/24.32 |
| 5,585,238 | 12/1996 | Ligon et al. | 435/6 |
| 5,622,827 | 4/1997 | McAllister et al. | 435/6 |
| 5,627,275 | 5/1997 | Roll | 536/23.7 |
| 5,631,132 | 5/1997 | Lott et al. | 435/6 |
| 5,635,353 | 6/1997 | Lott et al. | 435/6 |

OTHER PUBLICATIONS

Current Science, vol. 71, No. 6, Sep. 26, 1996, "PCR–Based Detection of Listeria Monocytogenes in Dairy Foods", S.K. Sood et al.

Methods in Molecular Biology, vol. 50, 1996, "ITS–RFLP Matching for Identification of Fungi", M. Gardes et al., pp. 177–186.

Applied and Environmental Microbiology, Aug. 1996, pp. 2947–2952, "Single–Strand Conformation Polymorphism Analysis of PCR–Amplified Ribosomal DNA Internal . . . Flavi", Y. Kumeda et al.

Molecular Ecology, 1993, vol. 2, pp. 113–118, "ITS Primers with Enhanced Specificity for Basidiomycetes–Application to the Identification of Mycorrhizae and Rusts", M. Gardes et al.

Applied and Environment Microbiology, Nov. 1996, pp. 4026–4031, "Identification of Root Rot Fungi in Nursery Seedlings . . . PCR", R.C. Hamelin et al.

Can. J. Bot., 72:342–346, 1994, Univ. of Guelp, Guelph, Ontario, CA, "Detection of Leptosphaeria korrae with the Polymerase Chain Reaction . . . spacers", D. O'Gorman et al.

Applied and Environmental Microbiology, Apr. 1995, pp. 1323–1330, "Development of Primer Sets Designed for Use with the PCR . . . Ascomycetes", Glass et al.

PCR Protocols: A Guide to Methods and Applications, "Amplification and Direct Sequencing of Fungal Ribosomal . . . Phylogenetics", T.J. White et al., 1990, pp. 315–322.

Molecular Plant–Microbe Interactions, vol. 9, No. 2, pp. 125–138, 1996, "Relationships Among Pathogenic and Non-pathogenic Isolates . . . DNA", D.J. Appel et al.

Methods in Molecular Biology, vol. 50: Species Diagnostics and Protocols, "Specific PCR Printers for Identification . . . Fungi", Luc Simon, 1996, pp. 187–192.

Applied and Environmental Microbiology, Dec. 1994, pp. 4324–4331, "PCR Primers that allow Intergeneric Differentiation . . . Verticilliumspp.", K.N. Li et al.

1996 BCPC Symposium Proceedings No. 65, "Detection of Phytoplasmas Associated with Pear Psyllids by Polymerase Chain Reaction", D.L. Davies et al., pp. 67–72.

Journal of Clinical Microbiology, Dec. 1995, pp. 3216–3220, "PCR and Single–Strand Conformational Polymorphism for Recognition . . . Fungi", T.J. Walsh et al.

Molecular and Cellular Probes, 1994, 8, pp. 215–222, "Detection of Candidemia by Polymerase Chain Reaction", K.H. Rand et al.

Applied and Environmental Microbiology, Feb. 1994, pp. 637–640, "Detection of Alcohol–Tolerant Hiochi Bacteria by PCR", T. Nakagawa et al.

Can. J. Microbiol. 42, pp. 1155–1162, 1996, "Genus– and Species–Specific Detection of Listeria monocytogenes using Polymerase Chain Reaction . . . Operon", T. Graham et al.

Journal of Medical and Veterinary Mycology, 1994, 32, pp. 115–122, "Rapid Presumptive Identification of Medically Relevant Yeasts . . . Analysis", M. Maiwald et al.

Journal of Medical and Veterinary Mycology, 1996, 34, pp. 251–258, "Assessment of a PCR Technique for the Detection . . . Neoformans", C. Prariyachatigul et al.

Journal of Applied Bacteriology, 1996, 80, pp. 244–251, "Detection of Salmonella Typhi by Polymerase Chain Reaction", Q. Zhu et al.

Applied and Environmental Microbiology, Aug. 1996, pp. 2988–2993, "Phytoplasma–Specific PCR Primers Based on Sequences . . . Region", C.D. Smart et al.

Plant Dis., 80:1170–1174, 1996, "Use of Unique RNA Sequence–Specific Oligonucleotide Primers . . . Strains", M.E. Omunyin et al.

Plant Dis., 80:1189–1192, 1996, "PCR Amplification from a Homology of the bE Mating–Type . . . DNA", H.H. Albert.

Applied and Environmental Microbiology, Dec. 1996, pp. 4514–4520, "PCR Differentiation of Commercial Yeast Strains . . . Primers", M. De Barros Lopes et al.

(List continued on next page.)

*Primary Examiner*—Carla J. Myers
*Attorney, Agent, or Firm*—Burns, Doane, Swecker & Mathis, L.L.P.

[57] ABSTRACT

Unique DNA sequences are provided which are useful in identifying different pathogenic fungi, such as those which infect grape plants. These unique DNA sequences can be used to provide oligonucleotide primers in PCR based analysis for the identification of fungal pathogens. The DNA sequences of the present invention include the internal transcribed spacer (ITS) of the ribosomal RNA gene regions of particular fungal pathogens, as well as oligonucleotide primers which are derived from these regions which are capable of identifying the particular pathogen.

23 Claims, No Drawings

OTHER PUBLICATIONS

Applied and Environmental Microbiology, Oct. 1996, pp. 3557–3559, "The Oligonucleotide Probe Database", E. Wheeler Alm, et al.

Applied and Environmental Microbiology, Jul. 1995, pp. 2809–2810, "Detection of an Arbuscular Mycorrhizal Fungus in Roots . . . PCR", R. Di Bonita et al.

Applied and Environmental Microbiology, Jul. 1995, pp. 2802–2805, "PCR Detection of the Lactocin S Structural Gene . . . Meat", J.M. Rodriguez et al.

Marine Pollution Bulletin, pp. 317–324, 1995, "Co–detection of Three Species of Water–Borne Bacteria by Multiplex PCR", R.Y.C. Kong et al.

Phytopathology, vol. 85, No. 8, pp. 913–917, 1995, "A Polymerase Chain Reaction–Based Procedure for Detection . . . Fescue", R.P. Doss et al.

Microbiol. Res., 1995, 150, pp. 379–385, "Application of the PCR Technique to Detect Phytophthora Infestans in Potato Tubers and Leaves", F. Niepold.

Phytopathology, 86:361–366, 1996, "A Rapid and Sensitive PCR–Based Assay for Concurrent Detection of Bacteria . . . Seed", P. Audy et al.

Letters in Applied Microbiology, 1990, 11, pp. 158–162, "Detection of Listeria Species and Listeria Monocytogenes . . . Reaction", P.M. Border et al.

Applied and Environmental Microbiology, Mar. 1996, pp. 998–1003, "Detection of Dekkera–Brettanomyces Strains in Sherry . . . Method", J. Ignacio Ibeas.

The Journal of Urology, vol. 156, pp. 154–156, Jul. 1996, "Early Identification of Candiduria by Polymerase Chain Reaction in High Risk Patients", P. Muncan et al.

Mycoses, 36, 171–179, 1993, "Identification of Clinical Strains of Candida Albicans by DNA Fingerprinting with the Polymerase Chain Reaction", G. Schönian et al.

Journal of Fermentation and Bioengineering, vol. 77, No. 2, 137–143, 1994, "Possible Use of a Polymerase Chain Reaction Method . . . Beef", Hau–Yang Tsen et al.

J. Vet Med. Sci., 58(9):881–884, 1996, "Detection of Salmonella DNA i n Chicken Embryos and Environmental Samples . . . Reaction", L.M. Tuchili et al.

Mazzola et al., Virulence of Rhizoctonia oryzae and R. solani AG–8 on Wheat and Detection of R. oryzae in Plant Tissue by PRC:, Phytopathology, 86:354–360, 1996.

M.V. Carter et al, "An annotated host list and bibliography of *Eutypa armeniacae*", Review of Plant Pathology, 62(7), 1983.

J. W. Fell, "Rapid identification of yeast species using three primers in a polymerase chain reaction", Molecular Marine Biol. and Biotechnol., 2(3):174–180, 1993.

J. W. Fell, "rDNA targeted oligonucleotide primers for the identification of pathogenic yeasts in a polymerase chain reaction", J. of Industrial Microbiol., 14:475–477, 1995.

F. Lavallée et al, "PCR and DNA Fingerprinting used as Quality Control in the Production of Wine Yeast Strains", Am. J. Enol. Vitic., 45(1):86–91, 1994.

E. Lieckfeldt et al, "Rapid identification and differentiation of yeasts by DNA and PCR fingerprinting", J. Basic Microbiol., 33(6):413–426, 1993.

F. Ness et al., "Identification of Yeast Strains using the Polymerase Chain Reaction", J. Sci. Food Agric., 62:89–94, 1993.

G. P. Casey et al, "Evaluation of Recent Techniques used to Identify Individual Strains of Saccharomyces Yeasts", ASBC Journal, 48(3):100–106, 1990.

R. Degré et al, "Wine Yeasts Strain Identification", Am. J. Enol. Vitic., 40(4):309–315, 1989.

J. M. Guillamón et al, "Characterization of Wine Yeast Strains of the Saccharomyces Genus on the Basis of Molecular Markers . . . Origin", System Appl. Microbiol., 19:122–132, 1996.

S.S. Možina et al, "Identification of Saccharomyces sensu stricto and Torulaspora yeasts by PCR ribotyping", Letters in Appl. Microbiol., 24:311–315, 1997.

D. Paffetti et al, "DNA fingerprinting by random amplified polymorphic DNA and restriction fragment length polymorphism . . . for yeast typing", Res. Microbiol., 146:587–594, 1995.

C.J. Panchal et al, "A Rapid, Simple and Reliable Method of Differentiating Brewing Yeast Strains based on DNA Restiction Patterns", J. Inst. Brew., 93:325–327, 1987.

A. Querol et al., "A Comparative Study of Different Methods of Yeast Strain Characterization", System Appl. Microbiol., 15:439–446, 1992.

P. Hoeben et al, "An approach to yeast classification by mapping mitochondrial DNA from Dekkera/Brettanomyces and Eeniella genera", Curr. Genet, 10:371–379, 1986.

F. Vezinhet et al, "Chromosomal DNA patterns and mitochondrial DNA polymorphism as tools for . . . *Saccharomyces cerevisiae*", Appl. Microbiol. Biotechnol., 32:568–571, 1990.

F. Vezinhet et al, "Ecological Survey of Wine Yeast Strains by Molecular Methods of Identification", Am. J. Enol. Vitic., 43(1):83–86, 1992.

A. Vaughan–Martini et al, Differential killer sensitivity as a tool for fingerprinting wine–yeast strains of *Saccharomyces cerevisiae*, J. of Industrial Microbiol., 17:124–127, 1996.

Peros et al. Phytopathology, 87: 799–804, Aug. 1997.

Rehner et al. Journal of Canadian Botany 72: 1666–1674, 1994.

Evans et al. GenBank Accession No. B00803, Jun. 1996.

Evans et al. GenBank Accession No. B04605, Jun. 1996.

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 605 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GGAAGTAAAA GTCGTAACAA GGTCTCCGTT GGTGAACCAG CGGAGGGATC ATTAAAGAGT      60
AGTTTTTACA ACAACTCCAA ACCCATGTGA ACTTACCTAT GTTGCCTCGG CGGGGAAACT     120
ACCCGGTAGC TACCCTGTAG CTACCCTGTA AGGAATACTC GTCGACGGAC CATTAAACTC     180
TGTTTTTCTA TGAAACTTCT GAGTGTTTTA ACTTAATAAA TTAAAACTTT CAACAACGGA     240
TCTCTTGGTT CTGGCATCGA TGAAGAACGC AGCGAAATGC GATAAGTAAT GTGAATTGCA     300
GAATTCAGTG AATCATCGAA TCTTTGAACG CACATTGCGC CCATTAGTAT TCTAGTGGGC     360
ATGCCTGTTC GAGCGTCATT TCGACCATCA AGCCCTATTT GCTTGGCGTT GGGAGCTTAC     420
CCTGCAGTTG CGGGATAACT CCTCAAATAT ATTGGCGGAG TCGCGGAGAC CCTAAGCGTA     480
GTAATTCTTC TCGCTTTAGT AGTGTTAACG CTGGCATCTG GCCACTAAAC CCCTAATTTT     540
TATAGGTTTG ACCTCGGATC AGGTAGGAAT ACCCGCTGAA CTTAAGCATA TCAATAAGCG     600
GAGGA                                                                605
```

(2) INFORMATION FOR SEQ ID NO:2:

(i) SEQUENCE CHARACTERISTICS:
      (A) LENGTH: 617 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GGAAGTAAAA GTCGTAACAA GGTCTCCGTT GGTGAACCAG CGGAGGGATC ATTACAGAGT      60
TACCTAACTC CAAACCCATG TGAACTTACC TATGTTGCCT CGGCGGGGAA GCCTACCCGG     120
TACCTACCCT GTAGCTACCC GGGAGCGAGC TACCCTGTAG CCCGCTGCAG GCCTACCCGC     180
CGGTGGACAC TTAAACTCTT GTTTTTTTAG TGATTATCTG AGTGTTTATA CTTAATAAGT     240
TAAAACTTTC AACAACGGAT CTCTTGGTTC TGGCATCGAT GAAGAACGCA GCGAAATGCG     300
ATAAGTAATG TGAATTGCAG AATTCAGTGA ATCATCGAAT CTTTGAACGC ACATTGCGCC     360
CATTAGTATT CTAGTGGGCA TGCCTGTTCG AGCGTCATTT CGACCTTCAA GCCCTAGCTG     420
CTTGGTGTTG GGAGCCTATC TCCGGATAGC TCCTCAAAAG CATTGGCGGA GTCGCGGTGA     480
CCCCAAGCGT AGTAATTCTT CTCGCTTTAG TGTGTCACG GCTGACGTCT TGCCGTTAAA     540
CCCCCAATTT TTTAAATGGT TGACCTCGGA TCAGGTAGGA ATACCCGCTG AACTTAAGCA     600
TATCAATAAG CGGAGGA                                                   617
```

(2) INFORMATION FOR SEQ ID NO:3:

(i) SEQUENCE CHARACTERISTICS:
    (A) LENGTH: 608 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

```
GGAAGTAAAA GTCGTAACAA GGTCTCCGTT GGTGAACCAG CGGAGGGATC ATTGCTGGAA    60

CGCGCCCCAG GCGCACCCAG AAACCCTTTG TGAACTTATA CCTTACTGTT GCCTCGGCGC   120

TAGCTGGTCC TTCGGGGCCC CTCACCCCCG GGTGTTGAGA CAGCCCGCCG GCGGCCAACC   180

CAACTCTTGT TTTTACACTG AAACTCTGAG AATAAAACAT AAATGAATCA AAACTTTCAA   240

CAACGGATCT CTTGGTTCTG GCATCGATGA AGAACGCAGC GAAATGCGAT AAGTAATGTG   300

AATTGCAGAA TTCAGTGAAT CATCGAATCT TTGAACGCAC ATTGCGCCCT CTGGTATTCC   360

GGAGGGCATG CCTGTTCGAG CGTCATTTCA ACCCTCAAGC CTGGCTTGGT GATGGGCAC    420

TGCTTCTTAC CCAAGGAGCA GGCCCTGAAA TTCAGTGGCG AGCTCGCCAG GACCCCGAGC   480

GCAGTAGTTA AACCCTCGCT CTGGAAGGCC CTGGCGGTGC CCTGCCGTTA AACCCCCAAC   540

TTCTGAAAAT TTGACCTCGG ATCAGGTAGG AATACCCGCT GAACTTAAGC ATATCAATAA   600

GCGGAGGA                                                           608
```

(2) INFORMATION FOR SEQ ID NO:4:

(i) SEQUENCE CHARACTERISTICS:
    (A) LENGTH: 611 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

```
GGAAGTAAAA GTCGTAACAA GGTCTCCGTT GGTGAACCAG CGGAGGGATC ATTGCTGGAA    60

CGCGCCCCTG GCGCACCCAG AAACCCTTTG TGAACTCATA CCTTACCGTT GCCTCGGCGC   120

AGGCCGGCCC CCCTGGGGG GCCCCTCGGA GACGAGGAGC AGGCCCGCCG GCGGCCAAGT    180

TAACTCTTGT TTTTACACTG AAACTCTGAG AAACAAAACA CAAATGAATC AAAACTTTCA   240

ACAACGGATC TCTTGGTTCT GGCATCGATG AAGAACGCAG CGAAATGCGA TAAGTAATGT   300

GAATTGCAGA ATTCAGTGAA TCATCGAATC TTTGAACGCA CATTGCGCCC TCTGGTATTC   360

CGGAGGGCAT GCCTGTTCGA GCGTCATTTC AACCCTCAAG CCTGGCTTGG TGATGGGCA    420

CTGCTCCCCC CCCCGGGGAG CAGGCCCTGA ATCCAGTGG CGAGCTCGCC AGGACCCCGA    480

GCGCAGTAGT TAAACCCTCG CTCCGGGAGG CCCTGGCGGT GCCCTGCCGT TAAACCCCCA   540

ACTTCTGAAA GTTTGACCTC GGATCAGGTA GGAATACCCG CTGAACTTAA AGCATATCAA   600

TAAGCGGAGG A                                                       611
```

(2) INFORMATION FOR SEQ ID NO:5:

(i) SEQUENCE CHARACTERISTICS:
    (A) LENGTH: 568 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

| GGAAGTAAAA | GTCGTAACAA | GGTTTCCGTA | GGTGAACCTG | CGGAAGGATC | ATTACCGAGT | 60 |
| TTTCGGGCTT | CGGCTCGACT | CTCCCACCCT | TTGTGAACGT | ACCTCTGTTG | CTTTGGCGGC | 120 |
| TCCGGCCGCC | AAAGGACCTC | CAAACTCCAG | TCAGTAAACG | CAGACGTCTG | ATAAACAAGT | 180 |
| TAATAAACTA | AAACTTTCAA | CAACGGATCT | CTTGGTTCTG | GCATCGATGA | AGAACGCAGC | 240 |
| GAAATGCGAT | AAGTAATGTG | AATTGCAGAA | TTCAGTGAAT | CATCGAATCT | TTGAACGCAC | 300 |
| ATTGCGCCCC | TTGGTATTCC | GGGGGGCATG | CCTGTTCGAG | CGTCATTACA | ACCCTCAAGC | 360 |
| TCTGCTTGGA | ATTGGGCACC | GTCCTCACTG | CGGACGCGCC | TCGAAGACCT | CGGCGGTGGC | 420 |
| TGTTCAGCCC | TCAAGCGTAG | TAGAATACAC | CTCGCTTTGG | AGTGGTTGGC | GTCGCCCGCC | 480 |
| GGACGAACCT | TCTGAACTTT | TCTCAAGGTT | GACCTCGGAT | CAGGTAGGGA | TACCCGCTGA | 540 |
| ACTTAAGCAT | ATCAATAAGC | GGAGGAAA | | | | 568 |

(2) INFORMATION FOR SEQ ID NO:6:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

| AAGAGTAGTT | TTTACAACAA | CTCCAAACCC | ATGTGAACTT | ACCTATGTTG | CCTCGGCGGG | 60 |
| GAAACTACCC | GGTAGCTACC | CTGTAGCTAC | CCTGTAAGGA | ATACTCGTCG | ACGGACCATT | 120 |
| AAACTCTGTT | TTTCTATGAA | ACTTCTGAGT | GTTTTAACTT | AATAAATTA | | 169 |

(2) INFORMATION FOR SEQ ID NO:7:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| CGACCATCAA | GCCCTATTTG | CTTGGCGTTG | GGAGCTTACC | CTGCAGTTGC | GGGATAACTC | 60 |
| CTCAAATATA | TTGGCGGAGT | CGCGGAGACC | CTAAGCGTAG | TAATTCTTCT | CGCTTTAGTA | 120 |
| GTGTTAACGC | TGGCATCTGG | CCACTAAACC | CCTAATTTTT | ATAGGT | | 166 |

(2) INFORMATION FOR SEQ ID NO:8:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| CAGAGTTACC | TAACTCCAAA | CCCATGTGAA | CTTACCTATG | TTGCCTCGGC | GGGGAAGCTT | 60 |
| ACCCGGTACC | TACCCTGTAG | CTACCCGGGA | GCGAGCTACC | CTGTAGCCCG | CTGCAGGCCT | 120 |

```
ACCCGCCGGT GGACACTTAA ACTCTTGTTT TTTTAGTGAT TATCTGAGTG TTTATACTTA    180

ATAAGTTA                                                             188

(2) INFORMATION FOR SEQ ID NO:9:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGACCTTCAA GCCCTAGCTG CTTGGTGTTG GGAGCCTATC TCCGGATAGC TCCTCAAAAG     60

CATTGGCGGA GTCGCGGTGA CCCCAAGCGT AGTAATTCTT CTCGCTTTAG GTGTGTCACG    120

GCTGACGTCT TGCCGTTAAA CCCCCAATTT TTTAAATGG                           159

(2) INFORMATION FOR SEQ ID NO:10:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTGGAACGCG CCCCAGGCGC ACCCAGAAAC CCTTTGTGAA CTTATACCTT ACTGTTGCCT     60

CGGCGCTAGC TGGTCCTTCG GGGCCCCTCA CCCCCGGGTG TTGAGACAGC CCGCCGGCGG    120

CCAACCCAAC TCTTGTTTTT ACACTGAAAC TCTGAGAATA AAACATAAAT GAATCA        176

(2) INFORMATION FOR SEQ ID NO:11:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CAACCCTCAA GCCTGGCTTG GTGATGGGGC ACTGCTTCTT ACCCAAGGAG CAGGCCCTGA     60

AATTCAGTGG CGAGCTCGCC AGGACCCCGA GCGCAGTAGT TAAACCCTCG CTCTGGAAGG    120

CCCTGGCGGT GCCCTGCCGT TAAACCCCCA ACTTCTGAAA AT                      162

(2) INFORMATION FOR SEQ ID NO:12:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CTGGAACGCG CCCCTGGCGC ACCCAGAAAC CCTTTGTGAA CTCATACCTT ACCGTTGCCT     60

CGGCGCAGGC CGGCCCCCCC TGGGGGGCCC CTCGGAGACG AGGAGCAGGC CCGCCGGCGG    120

CCAAGTTAAC TCTTGTTTTT ACACTGAAAC TCTGAGAAAC AAAACACAAA TGAATCA       177
```

(2) INFORMATION FOR SEQ ID NO:13:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CAACCCTCAA GCCTGGCTTG GTGATGGGGC ACTGCTCCCC CCCCCGGGGA GCAGGCCCTG     60

AAATCCAGTG GCGAGCTCGC CAGGACCCCG AGCGCAGTAG TTAAACCCTC GCTCCGGGAG    120

GCCCTGGCGG TGCCCTGCCG TTAAACCCCC AACTTCTGAA AGT                     163
```

(2) INFORMATION FOR SEQ ID NO:14:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
CCGAGTTTTC GGGCTTCGGC TCGACTCTCC CACCCTTTGT GAACGTACCT CTGTTGCTTT     60

GGCGGCTCCG GCCGCCAAAG GACCTCCAAA CTCCAGTCAG TAAACGCAGA CGTCTGATAA    120

ACAAGTTAAT AAACTA                                                    136
```

(2) INFORMATION FOR SEQ ID NO:15:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CAACCCTCAA GCTCTGCTTG GAATTGGGCA CCGTCCTCAC TGCGGACGCG CCTCGAAGAC     60

CTCGGCGGTG GCTGTTCAGC CCTCAAGCGT AGTAGAATAC ACCTCGCTTT GGAGTGGTTG    120

GCGTCGCCCG CCGGACGAAC CTTCTGAACT TTTCTCAAGG                          160
```

(2) INFORMATION FOR SEQ ID NO:16:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GGCGGGGAAA CTACCCGGTA GCTACCCTGT AGCTACCCTG TAAGGAATAC TCGTCGACGG     60

ACCAT                                                                 65
```

(2) INFORMATION FOR SEQ ID NO:17:

(i) SEQUENCE CHARACTERISTICS:
        (A) LENGTH: 61 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:17:

GACTCCGCCA ATATATTTGA GGAGTTATCC CGCAACTGCA GGGTAAGCTC CCAACGCCAA      60

G                                                                    61

(2) INFORMATION FOR SEQ ID NO:18:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

TACCTACCCT GTAGCTACCC GGGAGCGAGC TACCCTGTAG CCCGCTGCAG GCCTACCCGC      60

C                                                                    61

(2) INFORMATION FOR SEQ ID NO:19:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

AGAATTACTA CGCTTGGGGT CACCGCGACT CCGCCAATGC TTTTGAGGAG CTATCCGGAG      60

ATAGGCTCCC AACACCAAGC AGCTAGGGC                                       89

(2) INFORMATION FOR SEQ ID NO:20:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

AGCCCGCCGG CGGCCAACCC AACTCTTGTT TTTACACTGA AACTCTGAGA ATAAAACATA      60

A                                                                    61

(2) INFORMATION FOR SEQ ID NO:21:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

GGTTTAACTA CTGCGCTCGG GGTCCTGGCG AGCTCGCCAC TGAATTTCA                 49

(2) INFORMATION FOR SEQ ID NO:22:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GCGGCCAAGT TAACTCTTGT TTTTACACTG AAACTCTGAG AAACAAAACA CAAATGAATC    60

A                                                                   61
```

(2) INFORMATION FOR SEQ ID NO:23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGGTTTAACT ACTGCGCTCG GGGTCCTGGC GAGCTCGCCA CTGGATTTCA              50
```

(2) INFORMATION FOR SEQ ID NO:24:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
CCGAGTTTTC GGGCTTCGGC TCGACTCTCC CACCCTTTGT GAACGTACCT C            51
```

(2) INFORMATION FOR SEQ ID NO:25:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
CCGAGGTCTT TGAGGCGCGT CCGCAGTGAG GACGGTGCCC AATTCCAAGC              50
```

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
GCTACCCTGT AGCTACCCTG TAAGG                                         25
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGAGTTATCC CGCAACTGCA G                        21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GGGAGCGAGC TACCCTGTAG C                        21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

AGCTATCCGG AGATAGGCTC C                        21

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CACCGCGACT CCGCC                              15

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

AACTCTTGTT TTTACACTGA A                        21

(2) INFORMATION FOR SEQ ID NO:32:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GGTCCTGGCG AGCT                                          14

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TTTTACACTG AAACTCTGAG AA                                22

(2) INFORMATION FOR SEQ ID NO:34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

GGGTCCTGGC GAGCT                                       15

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

TCGGCTCGAC TCTCCC                                    16

(2) INFORMATION FOR SEQ ID NO:36:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CGCGTCCGCA GTGAG                                       15

-continued (2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
GGAAGTAAAA GTCGTAACAA GG                                            22
```

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
TCCTCCGCTT ATTGATATGC                                               20
```

DETECTION OF FUNGAL PATHOGENS

FIELD OF THE INVENTION

The present invention relates to assays to detect pathogenic fungi.

DESCRIPTION OF THE RELATED ART

Significant crop damage to grape plants is caused by fungal pathogens. Prompt and accurate diagnosis of the causal agent is important to effectively combat such pathogens. In the past, traditional culture techniques have been used to detect and identify fungal pathogens. Recently, however, DNA-based methods of identifying fungi have become available.

Polymerase chain reaction (PCR)-based techniques have been used to detect pathogens in infected animal tissues. This technique has also been applied to detect plant pathogens. For example, PCR has been used to detect the presence of *Gaeumannomyces graminis* in infected wheat by amplification of sequences specific to the pathogen mitochondrial genome (Schlesser et al., *Applied and Environ. Microbiol.*, 57:533–556, 1991); and numerous races of *Gremmeniella abietina*, the causal agent of scleroderris canker in conifers, were distinguished by random amplified polymorphic DNA (i.e. RAPD) markers.

Ribosomal genes are suitable for use as molecular probe targets because of their high copy number. Non-transcribed and transcribed spacer sequences associated with ribosomal genes are usually poorly conserved and, thus, are advantageously used as target sequences for the detection of recent evolutionary divergence. Fungal rRNA genes are organized in units. Each unit encodes mature subunits of 18S, 5.8S, and 28S rRNA. The internal transcribed spacer (ITS) region lies between the 18S and 28S rRNA genes and contains two variable non-coding spacers (referred to as ITS1 and ITS2) and the 5.8S rRNA gene (White et al., 1990; In: *PCR Protocols*; Eds.: Innes et al.; pages 315–322). In addition, the transcriptional units are separated by non-transcribed spacer sequences (NTSs). The ITS and NTS sequences are particularly suitable for the detection of different fungal pathogens.

Kumeda et al (*Applied Environ. Micro.*, 62(8):2947–2952, 1996) describes use of PCR to amplify ribosomal DNA internal transcribed spacers in order to differentiate species of Aspergillus Section flavi. The ITS1-5.8S-ITS2 region was amplified using universal primers, and the PCR product analyzed by the principle of single-strand conformation polymorphism. In addition, Gardes et al (In: *Methods in Molecular Biology, Vol. 50:Species Diagnostics Protocols: PCR and Other Nucleic Acid Methods*, Ed. J. P. Clapp, Humana Press, Totowa, N.J., pp. 177–186) describes restriction fragment length polymorphism (RFLP) analysis of fungal ITS regions amplified by PCR.

The PCR amplification of fungal ITS has also been described using other than universal primers. These methods allow for more specificity in identifying classes of fungi, or particular species of fungi. Thus, Gardes and Bruns (*Molecular Ecology*, 2:113–118, 1993) identified ITS primers which allow differentiation of DNA from basidiomycetes against ascomycete DNA. Identification of specific species has been observed using PCR primers directed to unique sequences in the ITS1 and/or ITS2 regions of fungal pathogens. See, for example, Hamelin et al, *Applied Environ. Micro.*, 62(11):4026–4031, 1996; Mazzola et al, *Phytopathology*, 86(4):354–360, 1996; O'Gorman et al, *Can. J. Bot.*, 72:342–346, 1994; and U.S. Pat. No. 5,585,238 to Ligon et al.

The present invention addresses the problem of detecting and identifying fungal pathogens by PCR-based techniques.

SUMMARY OF THE INVENTION

The present invention is directed to the identification of different pathogenic fungi, particularly those which infect grape plants. The present invention provides DNA sequences which exhibit variability between different pathogenic fungi. In particular, the present invention identifies regions of DNA sequence located in the internal transcribed spacer (ITS) of the ribosomal RNA gene regions of various pathogenic fungi. Primers derived from the ITS can be used in polymerase chain reaction (PCR) based diagnostic assays to determine the presence or absence of specific pathogenic fungi in plants, including grape plants. The primers can also be used as molecular probes to detect the presence of target DNA.

Thus, in one aspect, the present invention provides an isolated double stranded nucleic acid of the full length ITS1 or ITS2 region of a fungal pathogen known to infect plants. More particularly, the DNA sequence is selected from among Sequence ID NOS: 6 to 15.

In another aspect, the present invention provides an oligonucleotide primer for identification of a fungal pathogen, wherein the primer is a divergent portion of the ITS1 or ITS2 region of a fungal pathogen known to infect plants. More particularly, the oligonucleotide primer is selected from among Sequence ID NOS: 26 to 36. Furthermore, the oligonucleotide primers may be selected from among sequences which contain one of SEQ ID NOS: 26 to 36 and from 1 to 15 nucleotides in the 5' and/or 3' direction of the corresponding Sequence ID NOS: 16 to 25. A pair of the foregoing oligonucleotide primers for use in the amplification-based detection of an ITS of a fungal pathogen which infects plants is also provided.

In yet another aspect, a method is provided for detection of a fungal pathogen which comprises: (a) obtaining DNA from an organism, or part thereof, infected with a pathogen, or from a fungal culture isolated from a symptomatic or asymptomatic diseased organism; (b) amplifying a part of the ITS of the fungal pathogen using the DNA as a template in a polymerase chain reaction with the aforementioned oligonucleotide primers; and (c) visualizing the amplified part of the ITS sequence to determine whether the fungal pathogen is present.

In still another aspect, kits are provided which are useful in detecting fungal pathogens.

BRIEF DESCRIPTION OF THE SEQUENCES IN THE SEQUENCE LISTING

SEQ ID NO: 1 DNA sequence for the internal transcribed spacer of *Eutypella vitis*.

SEQ ID NO: 2 DNA sequence for the internal transcribed spacer of *Eutypa lata*.

SEQ ID NO: 3 DNA sequence for the internal transcribed spacer of *Phomopsis viticola (variant 1)*.

SEQ ID NO: 4 DNA sequence for the internal transcribed spacer of *Phomopsis viticola (variant 2)*.

SEQ ID NO: 5 DNA sequence for the internal transcribed spacer of *Diplodia gossypina*.

SEQ ID NO: 6 DNA sequence for the ITS1 of *Eutypella vitis*.

SEQ ID NO: 7 DNA sequence for the ITS2 of *Eutypella vitis*.

SEQ ID NO: 8 DNA sequence for the ITS1 of *Eutypa lata*.

SEQ ID NO: 9 DNA sequence for the ITS2 of *Eutypa lata*.

SEQ ID NO: 10 DNA sequence for the ITS1 of *Phomopsis viticola* (variant 1).
SEQ ID NO: 11 DNA sequence for the ITS2 of *Phomopsis viticola* (variant 1).
SEQ ID NO: 12 DNA sequence for the ITS1 of *Phomopsis viticola* (variant 2).
SEQ ID NO: 13 DNA sequence for the ITS2 of *Phomopsis viticola* (variant 2).
SEQ ID NO: 14 DNA sequence for the ITS1 of *Diplodia gossypina*.
SEQ ID NO: 15 DNA sequence for the ITS2 of *Diplodia gossypina*.
SEQ ID NO: 16 Oligonucleotide Sequence EVUITS1.
SEQ ID NO: 17 Oligonucleotide Sequence EVLITS2.
SEQ ID NO: 18 Oligonucleotide Sequence ELUITS1.
SEQ ID NO: 19 Oligonucleotide Sequence ELLITS2.
SEQ ID NO: 20 Oligonucleotide Sequence PVUITS1a.
SEQ ID NO: 21 Oligonucleotide Sequence PVLITS2a.
SEQ ID NO: 22 Oligonucleotide Sequence PVUITS1b.
SEQ ID NO: 23 Oligonucleotide Sequence PVLITS2b.
SEQ ID NO: 24 Oligonucleotide Sequence DGUITS1.
SEQ ID NO: 25 Oligonucleotide Sequence DGLITS2.
SEQ ID NO: 26 Oligonucleotide Sequence EVU129.
SEQ ID NO: 27 Oligonucleotide Sequence EVL422.
SEQ ID NO: 28 Oligonucleotide Sequence ELU141.
SEQ ID NO: 29 Oligonucleotide Sequence ELL430.
SEQ ID NO: 30 Oligonucleotide Sequence ELL465.
SEQ ID NO: 31 Oligonucleotide Sequence PVU182.
SEQ ID NO: 32 Oligonucleotide Sequence PVL463.
SEQ ID NO: 33 Oligonucleotide Sequence PVU191.
SEQ ID NO: 34 Oligonucleotide Sequence PVL464.
SEQ ID NO: 35 Oligonucleotide Sequence DGU70.
SEQ ID NO: 36 Oligonucleotide Sequence DGL384.
SEQ ID NO: 37 Oligonucleotide Sequence ITS5.
SEQ ID NO: 38 Oligonucleotide Sequence ITS4.

DETAILED DESCRIPTION OF THE INVENTION

The present invention provides unique DNA sequences which are useful in identifying pathogenic fungi. These unique DNA sequences can be used as primers in PCR-based analysis for the identification of fungal pathogens, or as molecular probes to detect the presence of DNA from fungal pathogens. The DNA sequences of the present invention include the internal transcribed spacer (ITS) of the ribosomal RNA gene regions of specific fungal pathogens, as well as primers that are derived from these regions which are capable of identifying the particular pathogen.

The DNA sequences of the invention are from the ITS of the ribosomal RNA gene region of fungal pathogens known to infect plants. However, the present invention is not limited to detecting the presence of the pathogens in plants, i.e., the invention can be used to detect the presence of such pathogens in any infected organism. There is variability in the ITS DNA sequences from different pathogens. The ITS sequences can be aligned and compared. Primers can be designed based on regions within the ITS regions that contain the greatest differences in sequence among the fungal pathogens. The sequences and primers based on these sequences can be used to identify specific pathogens.

DNA sequences of particular interest include ITS DNA sequences from Eutypella sp., especially *Eutypella vitis*; Eutypa sp., especially *Eutypa lata*; Phomopsis sp., especially *Phomopsis viticola*; and Diplodia sp., especially *Diplodia gossypina*. The ITS DNA sequences, as well as primers of interest, are set forth in SEQUENCE ID NOS: 1–38. The sequences are useful in PCR-based identification of fungal pathogens.

Methods for use of the primer sequences of the invention in PCR analysis are well known in the art. For example, see U.S. Pat. Nos. 4,683,195; 4,683,202 and 5,585,238, the contents of all of which are hereby incorporated by reference.

The primer sequences of the invention can also be used as molecular probes to detect the presence of target DNA. The Tm for the primers ranges from about 48–58° C. at 50 mM salt. The hybridization temperature is approximately 5–10° C. below the melting temperature. Thus, the primers are hybridized to target DNA typically at a temperature ranging from about 43–55° C. Final wash conditions generally range from about 45–55° C. at about 36 mM salt concentration. Specific hybridization as used herein means the use of a final high stringency wash in about 0.2X SSPE (salt concentration of about 36 mM) at a temperature appropriate for the particular primer. 1X SSPE contains 10 mM $NaH_2PO_4$, 180 mM NaCl, 1 mM EDTA, pH 7.4.

The ITS DNA sequences of the present invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287; the contents of all of which are hereby incorporated by reference.

Alternatively, the ITS regions of interest can be identified by PCR amplification. Primers to amplify the entire ITS region can be designed according to White et al. (1990; In PCR Protocols; Eds.: Innes et al., pages 315–322, the contents of which are hereby incorporated by reference).

The ITS sequences were determined and the sequences were compared to locate divergences which might be useful to test in PCR to distinguish the different fungal pathogens. The sequences of the ITS regions which were determined are shown as Sequence ID NOS: 1 to 5. The DNA sequences for the ITS1 and ITS2 regions are shown as Sequence ID NOS: 6 to 15. From the identification of divergences, numerous primers were synthesized and tested in PCR-amplification. Purified pathogen DNA and DNA isolated from infected host plant tissue were used as templates for PCR-amplification. Thus, pairs of diagnostic primers were identified, i.e., those which identified one particular fungal pathogen species. Preferred primer combinations are able to distinguish between the different fungal pathogens in infected host tissue. Primer sequences are set forth in Sequence ID NOS: 26 to 36, with flanking sequences depicted in Sequence ID NOS: 16 to 25. Thus, while oligonucleotide primers selected from among Sequence ID NOS: 26 to 36 are preferred, primers may also be used which contain at least 10 contiguous nucleotide bases from one of SEQ ID NOS: 26 to 36. Additionally, primers may be used which contain at least 10 contiguous nucleotide bases from one of SEQ ID NOS: 26 to 36 contiguous with 1 to 15 nucleotide bases in the 5' and/or 3' direction of corresponding SEQ ID NOS: 16 to 25, and primers of 10 nucleotide bases or longer which contain at least 5 contiguous nucleotide bases from one of SEQ ID NOS: 26 to 36 contiguous with from 1 to 15 nucleotide bases in the 5' and/or 3' direction of corresponding SEQ ID NOS: 16 to 25.

The present invention provides numerous diagnostic primer combinations. The primers of the invention are designed based on sequence differences among the fungal ITS regions. A minimum of one base pair difference between sequences can permit design of a discriminatory primer. In general, primers should have a theoretical melting temperature between about 55° C. to about 65° C. to achieve good sensitivity, and should be void of significant secondary structure and 3' overlaps between primer combinations. Primers are generally at least about 10 nucleotide bases, more preferably at least about 15 to about 20 nucleotide bases.

The oligonucleotide primers of the present invention are particularly useful in detecting infection of grape plants with fungal pathogens, in particular, fungal pathogens selected from among *Eutypella vitis, Eutypa lata, Phomopsis viticola* and *Diplodia gossypina*. However, the primers of the present invention can also be used to detect infection by the foregoing fungal pathogens in any organism which will act as a host. In the case of plants, for example, *Eutypa lata* (also known as *Eutypa armeniacae*) can infect plants other than grape plants, including apricot, black currant, red currant, almond, walnut, apple, prune, peach, pear, European plum, gooseberry and lemon plants. See Carter et al (1983) *Review of Plant Pathology*, Vol. 62, No. 7, incorporated herein by reference.

The present invention also relates to the preparation of "kits" containing elements for detecting fungal pathogens. Such a kit may comprise a carrier to receive therein one or more containers, such as tubes or vials. Unlabeled or detectably labeled oligonucleotide primers may be contained in one or more of the containers. The oligonucleotide primers may be present in lyophilized form, or in an appropriate buffer. One or more enzymes or reagents for use in PCR reactions may be contained in one or more of the containers. The enzymes or reagents may be present alone or in admixture, and in lyophilized form or in appropriate buffers. The kit may also contain any other component necessary for carrying out the present invention, such as buffers, extraction agents, enzymes, pipettes, plates, nucleic acids, nucleoside triphosphates, filter paper, gel materials, transfer materials, and autoradiography supplies.

The examples below illustrate typical experimental protocols which can be used in the isolation of ITS sequences, the selection of suitable primer sequences, the testing of primers for selective and diagnostic efficacy, and the use of such primers to detect the presence of a fungal pathogen. Such examples are provided by way of illustration and not by way of limitation.

EXAMPLES

Example 1

Culture of Fungal Isolates and Genomic DNA Extraction

Viable fungal isolates of *Eutypella vitis, Eutypa lata, Phomopsis viticola*, and *Diplodia gossypina* were obtained from the E. & J. Gallo Genetics Research Fungal Culture Collection. Fungi were grown in 40 ml of Malt Yeast Extract Broth in 250 ml flasks inoculated with mycelial fragments from two week-old, cultures grown on Malt Yeast Extract Agar (MYEA). Liquid cultures were incubated at room temperature for 14 days without shaking.

DNA was extracted as follows:
1. Collect 2–3 mycelial mats from culture flasks (250 ml flask/40 ml media). Grind mycelial mats using a mortar and pestle in the presence of liquid nitrogen. Transfer the powder to 45 ml polypropylene centrifuge tubes and add 15 ml of prewarmed extraction buffer (1X extraction buffer; 50 mM sodium ethylene diaminetetraacetic acid (EDTA), 100 mM tris-HCl (pH 8.0), 500 mM NaCl). Add 0.2% β-mercaptoethanol just prior to use. Mix by inversion and/or break up clumps with spatula.
2. Add 1.0 ml of 20% sodium dodecyl sulfate (SDS), mixing gently by inversion, incubate at 65° C. for 10 min.
3. Add 5.0 ml of 5.0 M potassium acetate and mix gently, but thoroughly, by inverting the tubes. Incubate in freezer for 20 min.
4. Centrifuge at 25000×g for 20 min at 4° C. Pour supernatant through a Miracloth® filter into a clean 35 ml Corex® centrifuge tube containing 10 ml ice-cold isopropanol; mix and incubate tubes in freezer for 30 min.
5. Spool out DNA on glass hooks or pellet by centrifugation at 20,000×g for 15 min. Gently pour off supernatant and lightly dry pellets by inverting over a paper towel for 10 min.
6. Resuspend pellets in 0.75 ml of TE (10 mM Tris_HCl, 1 mM EDTA). Transfer to a 1.7 ml microcentrifuge tube. Add 375 µl of phenol and 375 µl of chloroform: isoamyl alcohol (24:1). Shake the tubes until an emulsion forms. Spin the samples at 14,000 RPM for 10 min. Remove the aqueous (top) layer using a P1000® pipet and put into a new 1.7 ml microcentrifuge tube. Try not to pull off any of the cloudy/slimy interface between the upper and lower layers. Add 750 µl of chloroform: isoamyl alcohol (24:1) to the sample, mix well, and spin at 14,000 RPM for 10 min.
7. Remove the aqueous (top) layer and put into a 15 ml plastic centrifuge tube. Add DDH$_2$O to bring volume up to 2 ml and then add 2 ml of 5M NaCl. Mix well and add 8 ml of cold 100% ethanol. Mix gently and spool out the DNA using a glass hook. If the DNA cannot be recovered with a glass hook, spin at a low speed (2-3000 RPM) in the centrifuge. Dry the DNA and resuspend in 500 µl of DDH$_2$O.
8. Add 50 µl of 7.5 M ammonium acetate and 1100 µl of cold 100% ethanol. Mix well and place in-freezer for at least one h. Spin the samples at 14,000 RPM for 10 min and dry the pellet in the Speed-Vac®. Resuspend in 3–500 µl of DDH$_2$O.

Direct Amplification of DNA from Fungal Mycelia

1. Malt Yeast Extract Agar plates are inoculated with mycelia and grown for 2 weeks.
2. A sterile pipette tip is used to scrape a small amount of aerial mycelia off of the plate and deposited into a 250 µl microcentrifuge tube containing all of the components required for the polymerase chain reaction as stated in Example 6.

Example 2

Amplification and Sequencing of the Internal Transcribed Spacer (ITS) Regions An ~600 bp internal transcribed spacer region was amplified from genomic DNA isolated from 28 isolates of *Eutypa lata*, two isolates of *E. armeniacae*, three isolates of *Libertella viticola*, one isolate of *Eutypella vitis*, six isolates of *Phomopsis viticola*, and four isolates of *Diplodia gossypina* (see Table 1) using ITS5 (5'-GGAAGTAAAAGTCGTAACAAGG-3'; SEQ ID NO: 37) and ITS4 (5'-TCCTCCGCTTATTGATATGC-3'; SEQ ID NO: 38). The 50-µl reactions contained 5–20 ng of genomic template, 5 µch of GeneAmp® 10X Buffer II and MgCl$_2$ solution (PE Applied Biosystems, Foster City, Calif.; part no. N808-0161), 0.2 mM each of dATP, dCTP, dGTP, and dTTP (GeneAmp® dNTPs; PE Applied Biosystems, Foster City, Calif.; part no. N808-0007), ~25 pM/µl each of ITS5 and ITS4, and 2.5 Units AmpliTaq® DNA polymerase (PE Applied Biosystems; part no. N808-0161). Reactions were run for 35 cycles of 30 s at 94° C., 40 s at 58° C., and 2 min at 72° C., followed by a final elongation step at 72° C. for 10 min, on a Perkin Elmer GeneAmp® PCR System 9600 (PE Applied Biosystems). PCR products were purified using QIAquick® PCR Purification Kits (Qiagen Inc., Santa Clarita, Calif.) to remove any excess primers, nucleotides, and polymerases. Five microliters of the purified PCR products were run on a 1.2% agarose gel with 5 µl of pGEM-3Zf(+) double-stranded DNA Control Template (0.2 g/L, PE Applied Biosystems) to approximate concentrations. All products were sequenced using the primers ITS5 and ITS4 (see sequences above; White et al., 1990; In: *PCR Protocols*; Eds.: Innes et al. pp. 315–322). Sequencing was performed on an PE Applied Biosystems 377 Automated DNA Sequencer® using ABI PRISM™ Dye Terminator Cycle Sequencing Ready Reaction Kits® (PE Applied Biosystems; part no. 402079). Cycle sequencing products were run over Centri-Sep® spin columns (Princeton Separations, Inc., Adelphia, N.J.) to remove excess primers, dye-labeled terminators, nucleotides, and polymerases before being run on the automated sequencer.

Example 3

Selection of Species-Specific Primers

The ITS sequences of the *Eutypa lata, Eutypella vitis, Phomopsis viticola*, and *Diplodia gossypina* isolates were aligned and primers were designed using Oligo 5.0 (National Biosciences, Inc., Plymouth, Minn.) in regions of maximum sequence difference between the target species.

Example 4

Primer Synthesis

Primers were synthesized on an Applied Biosystems 394 DNA/RNA Synthesizer® using phosphoramidite chemistry.

Example 5

Extraction of DNA from Plant Tissue for Use with Diagnostic Primers

1. Excise 10 mg fresh weight of plant tissue. Place in a microcentrifuge tube with 100 µl of 0.5 N NaOH and grind for 30 s with a small, motor powered pestle.
2. Immediately transfer 5 µl of this extract to a microcentrifuge tube containing 495 µl of 100 mM Tris, pH 8.0.
3. Immediately mix the extract with the Tris by vortexing the tube contents. This is critical to prevent damage to the DNA. Use 1–2 µl of this mixture as the template DNA for PCR.

Example 6

Polymerase Chain Reaction Amplification

Polymerase chain reactions were performed with the GeneAmp® kit from PE Applied Biosystems (Foster City, Calif.; part no. N801-0055) using 50 mM KCl, 1.5 mM $MgCl_2$, 10 mM Tris, pH 8.3, containing 200 µM of each TTP, dATP, dCTP, and dGTP, 50 pM of each primer, 2.5 units of Taq polymerase and 25 ng of genomic DNA, or barely visible amount of mycelia, in a final volume of 50 µl. The following thermocycler program was used: initial denaturation at 94° C. for 2 min; 35 cycles of three temperatures consisting of denaturing at 94° C. for 30 s followed by annealing for 40 s at 45, 50, 55, 58, 60, or 62° C. and elongation for 2 min at 72° C.; then a final elongation step for 10 min at 72° C. The products were analyzed by loading 25 µl of each PCR sample on a 1.0% agarose gel and electrophoresing.

Example 7

Verification of Primer Specificity to Extracted fungal genomic DNA from Target Species.

Purified fungal genomic DNAs were obtained as described in Example 1 and PCR assayed as described in Example 6 using the species-specific primers. Different annealing temperatures were tested to determine the optimal temperature for PCR for individual primers. In cases with multiple species-specific primers, different primer combinations were used to determine the best primer combination and annealing temperature to amplify a single species-specific DNA fragment (Table 4). Species-specific amplification products were produced from primers designed from the ITS region between the 18S and 25S ribosomal DNA subunits of each fungal strain of interest.

Example 8

Determination of Cross-reactivity of Species-specific Primers with Non-target Species.

Purified fungal genomic DNAs obtained as described in Example 1 and/or direct amplification from mycelia as described in Example 1 were used with the PCR assay as described in Example 8 using the species-specific primers. Table 5 lists the results of the cross-reactivity tests with the species-specific primers and non-target fungal species. A 60° C. annealing temperature was sufficient to prevent cross-reactivity between species-specific primers and non-target species.

Example 9

Verification of Primer Specificity to Detect Presence of Grape Pathogenic Fungi in Plant Tissue DNA was isolated from woody and green plant tissue using the method outlined in Example 5. PCR was performed as described in Example 6. The species-specific primer combinations detected the target grape fungal pathogen in all plant tissues tested. Controls consisting of non-infected plant tissue tested negative for all species-specific primer pairs examined.

Example 10

Utilization of ITS Sequences as Diagnostic Probes to Hybridize with Target DNA i. Put chosen concentration of target DNA sample in 100 ul of TE, pH 7.0.
ii. Add 0.1 volume [10 µl] of 3.0 M NaOH, vortex to mix and incubate at 65° C. for 20 min. This destroys the RNA and denatures the DNA.
iii. Spin down condensation. Allow samples to cool to room temp. Neutralize by adding 1.0 volume [110 µl] of 2M ammonium acetate, pH 7.0, vortex to mix. Spin down to remove solution off of cap. Refrigerate until slot blot apparatus is ready.
iv. Apply to slot-blot apparatus according to manufacturers protocol; about 220 µl to slot blot.

v. Label ITS sequence probe according to kit manufacturer's recommendation.

vi. The blots are prehybridized in 1.0% BSA; 1 mM EDTA, 0.5 M NaHPO$_4$, pH 7.2, 7.0% sodium dodecyl sulfate for a minimum of two hr prior to adding the probe, and then hybridized for 16 hr at 45° C. Initial washes consist of two 30-min washes in 1X SSPE/0.1% SDS at 50° C. The blots are then transferred to a plastic tray and washed in 1X SSPE for one hr, at 50° C. with shaking. The final wash consisted of 15 min at 50° C. in 0.2X SSPE.

TABLE 1

Source of Test Isolates

| Isolate | Species | Origin | Source |
| --- | --- | --- | --- |
| ATCC #64171 | Eutypella vitis | Illinois | ATCC[1] |
| ATCC #28120 | Eutypa armeniacae | Australia | ATCC[1] |
| ATCC #28900 | Eutypa armeniacae | South Africa | ATCC[1] |
| B100 | Eutypa lata | California | G. Munkvold[2] |
| E101 | Eutypa lata | California | G. Munkvold[2] |
| E102 | Eutypa lata | California | G. Munkvold[2] |
| E103 | Eutypa lata | California | G. Munkvold[2] |
| E104 | Eutypa lata | California | G. Munkvold[2] |
| E105 | Eutypa lata | California | G. Munkvold[2] |
| E106 | Eutypa lata | California | G. Munkvold[2] |
| E107 | Eutypa lata | California | G. Munkvold[2] |
| E108 | Eutypa lata | California | G. Munkvold[2] |
| B109 | Eutypa lata | California | G. Munkvold[2] |
| E110 | Eutypa lata | California | G. Munkvold[2] |
| E111 | Eutypa lata | California | G. Munkvold[2] |
| E112 | Eutypa lata | California | G. Munkvold[2] |
| B113 | Eutypa lata | California | G. Munkvold[2] |
| E114 | Eutypa lata | California | G. Munkvold[2] |
| E115 | Eutypa lata | California | G. Munkvold[2] |
| E116 | Eutypa lata | California | G. Munkvold[2] |
| E117 | Eutypa lata | New York | G. Munkvold[2] |
| E118 | Eutypa lata | California | G. Munkvold[2] |
| E119 | Eutypa lata | California | G. Munkvold[2] |
| E120 | Eutypa lata | California | N. Irelan[3] |
| E121 | Eutypa lata | California | N. Irelan[3] |
| E122 | Eutypa lata | California | N. Irelan[3] |
| E123 | Eutypa lata | Michigan | G. Munkvold[2] |
| E124 | Eutypa lata | Michigan | G. Munkvold[2] |
| E125 | Eutypa lata | Italy | S. Di Marco[4] |
| E126 | Eutypa lata | California | G. Munkvold[2] |
| E127 | Eutypa lata | California | G. Munkvold[2] |
| L1 | Libertella viticola | Italy | S. Serra[5] |
| L2 | Libertella viticola | Italy | S. Serra[5] |
| L3 | Libertella viticola | Italy | S. Serra[5] |
| ATCC #12685 | Phomposis viticola | unknown | ATCC[1] |
| ATCC #28595 | Phomposis viticola | unknown | ATCC[1] |
| ATCC #28596 | Phomposis viticola | unknown | ATCC[1] |
| ATCC #38931 | Phomposis viticola | Australia | ATCC[1] |
| ATCC #48153 | Phomposis viticola | California | ATCC[1] |
| ATCC #76192 | Phomposis viticola | New York | ATCC[1] |
| ATCC #9055 | Diplodia gossypina | Unknown | ATCC[1] |
| ATCC #10936 | Diplodia gossypina | Florida | ATCC[1] |
| ATCC #1639 | Diplodia gossypina | Central America | ATCC[1] |
| ATCC #20571 | Diplodia gossypina | unknown | ATCC[1] |
| A150 | Aureobasidium sp. | California | GGRFCC[6] |
| A250 | Alternaria sp. | California | GGRFCC[6] |
| B002 | Botrytis cinerea | Italy | S. Di Marco[4] |
| C200 | Cladosporium sp. | California | GGRFCC[6] |
| F100 | Fusarium sp. | California | GGRFCC[6] |

[1]American Type Culture Collection, Rockville, Maryland USA
[2]Dr. Gary Munkvold, Dept. of Plant Pathology, Iowa State University, Ames, IA, USA
[3]Dr. Nancy Irelan, Genetics Research, E. & J. Gallo Winery, Modesto, CA, USA
[4]Dr. Stefano Di Marco, Consiglio Nazionale Delle Ricerche, Bologna, Italy
[5]Dr. Salvatorica Serra, Istituto Sperimentale per la Viticoltura, Conegliano, Italy
[6]Gallo Genetics Research Fungal Culture Collection, E. & J. Gallo Winery, Modesto, CA USA

TABLE 2

| Primer Template | Primer Name | Primer Sequence |
| --- | --- | --- |
| E. vitis | EVU129 | 5'-GCTACCCTGTAGCTACCCTGTAAGG-3' (SEQ ID NO: 26) |
| E. vitis | EVL422 | 5'-GGAGTTATCCCGCAAGTCCAG-3' (SEQ ID NO: 27) |
| E. lata | ELU141 | 5'-GGGAGCGAGCTACCCTGTAGC-3' (SEQ ID NO: 28) |
| E. lata | ELL430 | 5'-AGCTATCCGGAGATAGGCTCC-3' (SEQ ID NO: 29) |
| E. lata | ELL465 | 5'-CACCGCGACTCCGCC-3' (SEQ ID NO: 30) |
| P. viticola | PVU182 | 5'-AACTCTTGTTTTTACACTGAA-3' (SEQ ID NO: 31) |
| P. viticola | PVL463 | 5'-GGTCCTGGCGAGCT-3' (SEQ ID NO: 32) |
| P. viticola | PVU191 | 5'-TTTTACACTGAAACTCTGAGAA-3' (SEQ ID NO: 33) |
| P. viticola | PVL464 | 5'-GGGTCCTGGCGAGCT-3' (SEQ ID NO: 34) |
| D. gossypina | DGU70 | 5'-TCGGCTCGACTCTCCC-3' (SEQ ID NO: 35) |
| D. gossypina | DGL384 | 5'-CGCGTCCGCAGTGAG-3' (SEQ ID NO: 36) |
| 18S rDNA | ITS5 | 5'-GGAAGTAAAAGTCGTAACAAGG-3' (SEQ ID NO: 37) |
| 28S rDNA | ITS4 | 5'-TCCTCCGCTTATTGATATGC-3' (SEQ ID NO: 38) |

TABLE 3

ITS-derived diagnostic PCR primers

| Source of template DNA | 5' Primer | 3' Primer | Approximate size of amplified fragment (bp) |
| --- | --- | --- | --- |
| Eutypa lata | ELU141 | ELL430 | 310 |
|  | ELU141 | ELL465 | 338 |
|  | ITS5 | ELL430 | 472 |
|  | ITS5 | ELL465 | 501 |
|  | ELU141 | ITS4 | 497 |
| Eutypella vitis | EVU129 | EVL422 | 314 |
|  | ITS5 | EVL422 | 464 |
|  | EVU129 | ITS4 | 496 |
| Phomopsis viticola | PVU182 | PVL463 | 294 |
|  | PVU182 | PVL464 | 295 |
|  | PVU191 | PVL463 | 285 |
|  | PVU191 | PVL464 | 286 |
|  | ITS5 | PVL463 | 498 |
|  | ITS5 | PVL464 | 499 |
|  | PVU182 | ITS4 | 392 |
|  | PVU191 | ITS4 | 383 |
| Diplodia gossypina | DGU70 | DGL384 | 328 |
|  | ITS5 | DGL384 | 418 |
|  | DGU70 | ITS4 | 457 |

TABLE 4

Verification of species-specific primers to target species

| Target Species | Species-specific Primers | Temp (° C.) | Reaction |
|---|---|---|---|
| *Eutypella vitis* | EVU129/BVL422 | 54 | (+) |
| | | 58 | (+) |
| | | 60 | (+) |
| | | 62 | (+) |
| *Eutypa lata* | ELU141/ELL430 | 54 | (+) |
| | | 58 | (+) |
| | | 60 | (+) |
| | | 62 | (+) |
| | ELU14l/ELL465 | 54 | (+) |
| | | 58 | (+) |
| | | 60 | (+) |
| | | 62 | (+) |
| *Diplodia gossypina* | DGU70/DGL384 | 60 | (+) |
| *Phomopsis viticola* | PVU182/PVL463 | 60 | (+) |
| | PVU182/PVL464 | 60 | (+) |
| | PVU191/PVL463 | 60 | (+) |
| | PVU191/PVL464 | 60 | (+) |

TABLE 5

Cross-reactivity with species-specific primers and non-target species

| Target Species | Species-specific Primers | Temp (° C.) | Non-target Species | Reaction |
|---|---|---|---|---|
| *Eutypella vitis* | EVU129/EVL422 | 60 | *Eutypa lata* | (−) |
| | | 60 | *Libertella viticola* | (−) |
| | | 60 | *Phomopsis viticola* | (−) |
| | | 60 | *Diplodia gossypina* | (−) |
| *Eutypa lata* | ELU141/ELL430 | 62 | *Eutypella vitis* | (−) |
| | | 60 | *Eutypa armeniacae* | (+) |
| | | 60 | *Libertella viticola* | (+) |
| | | 60 | *Phomopsis viticola* | (−) |
| | | 60 | *Diplodia gossypina* | (−) |
| | | 60 | *Aureobasidium* sp. | (−) |
| | | 60 | *Cladosporium* sp. | (−) |
| | | 60 | *Fusarium* sp. | (−) |
| | | 60 | *Botrytis cinerea* | (−) |
| | | 60 | *Alternaria* sp. | (−) |
| | ELU141/ELL465 | 62 | *Eutypella vitis* | (−) |
| | | 60 | *Eutypa armeniacae* | (+) |
| | | 60 | *Libertella viticola* | (+) |
| | | 60 | *Phomopsis viticola* | (−) |
| | | 60 | *Diplodia gossypina* | (−) |
| | | 60 | *Aureobasidium* sp. | (−) |
| | | 60 | *Cladosporium* sp. | (−) |
| | | 60 | *Fusarium* sp. | (−) |
| | | 60 | *Botrytis cinerea* | (−) |
| | | 60 | *Alternaria* sp. | (−) |
| *Diplodia gossypina* | DGU70/DGL384 | 60 | *Phomopsis viticola* | (−) |
| | | 60 | *Eutypa lata* | (−) |
| *Phomopsis viticola* | PVU182/PVL463 | 60 | *Eutypa lata* | (−) |
| | | 60 | *Diplodia gossypina* | (−) |
| | PVU182/PVL464 | 60 | *Eutypa lata* | (−) |
| | | 60 | *Diplodia gossypina* | (−) |
| | PVU191/PVL463 | 60 | *Eutypa lata* | (−) |
| | | 60 | *Diplodia gossypina* | (−) |
| | PVU191/PVL464 | 60 | *Eutypa lata* | (−) |
| | | 60. | *Diplodia gossypina* | (−) |
| | | 60 | *Fusarium* sp. | (−) |

We claim:

1. An isolated double stranded nucleic acid selected from the group consisting of SEQ ID NOS: 6 to 10 and 12 to 15, and their complementary sequences.

2. An isolated nucleic acid which specifically hybridizes with the nucleic acid of claim 1.

3. An oligonucleotide sequence for identification of a fungal pathogen, wherein said sequence is selected from the group consisting of SEQ ID NOS: 16 to 25.

4. An oligonucleotide primer which is a fragment of the sequences according to claim 3, and which specifically hybridizes to the ITS1 or ITS2 of *Eutypella vitis, Eutypa lata, Phomopsis viticola,* or *Diplodia gossypina*.

5. An oligonucleotide primer for identification of a fungal pathogen, wherein said primer specifically amplifies at least a portion of the ITS1 region of SEQ ID NOS:6, 8, 10, 12 or 14 or at least a portion of the ITS2 region of SEQ ID NOS:7, 9, 11, 13 or 15, or which specifically amplifies at least a portion of the ITS region of a fungal pathogen selected from the group consisting of Eutypella sp. Eutypa sp. Phomopsis sp. and Diplodia sp. wherein said primer is selected from the group consisting of primers which contain at least 10 contiguous nucleotide bases from one of SEQ ID NOS: 26 to 36, primers which contain at least 10 contiguous nucleotide bases from one of SEQ ID NOS: 26 to 36 contiguous with 1 to 15 flanking nucleotide bases in the 5' and/or 3' direction of SEQ ID NOS: 16 to 25, and primers of 10 nucleotide bases or longer which contain at least 5 contiguous nucleotide bases from one of SEQ ID NOS: 26 to 36 contiguous with from 1 to 15 flanking nucleotide bases in the 5' and/or 3' direction of SEQ ID NOS: 16 to 25.

6. A pair of oligonucleotide primers for use in the amplification-based detection of an internal transcribed spacer sequence of a fungal pathogen, wherein said primers specifically amplify at least a portion of the ITS1 region of SEQ ID NOS:6, 8, 10, 12 or 14 or at least a portion of the ITS2 region of SEQ ID NOS:7, 9, 11, 13 or 15, or which specifically amplify at least a portion of the ITS region of a fungal pathogen selected from the group consisting of Eutypella sp. Eutypa sp. Phomopsis sp. and Diplodia sp., wherein the primers are selected from the group consisting of primers which contain at least 10 contiguous nucleotide bases from one of SEQ ID NOS: 26 to 36, primers which contain at least 10 contiguous nucleotide bases from one of SEQ ID NOS: 26 to 36 contiguous with 1 to 15 flanking nucleotide bases in the 5' and/or 3' direction of SEQ ID NOS: 16 to 25, and primers of 10 bases or longer which contain at least 5 contiguous nucleotide bases from one of SEQ ID NOS: 26 to 36 contiguous with from 1 to 15 flanking nucleotide bases in the 5' and/or 3' direction of SEQ ID NOS: 16 to 25.

7. The pair of oligonucleotide primers according to claim 6 which comprises SEQ ID NO: 26 and SEQ ID NO: 27.

8. The pair of oligonucleotide primers according to claim 6 which comprises SEQ ID NO: 28 and SEQ ID NO: 29.

9. The pair of oligonucleotide primers according to claim 6 which comprises SEQ ID NO: 28 and SEQ ID NO: 30.

10. The pair of oligonucleotide primers according to claim 6 which comprises SEQ ID NO: 31 and SEQ ID NO: 32.

11. The pair of oligonucleotide primers according to claim 6 which comprises SEQ ID NO: 33 and SEQ ID NO: 34.

12. The pair of oligonucleotide primers according to claim 6 which comprises SEQ ID NO: 35 and SEQ ID NO: 36.

13. A method for detection of a fungal pathogen comprising:

(a) obtaining DNA from an organism, or part thereof, infected with a pathogen, or from a fungal culture isolated from a symptomatic or asymptomatic diseased organism;

(b) amplifying a part of the internal transcribed spacer sequence of said fungal pathogen using said DNA as a template in a polymerase chain reaction with a pair of oligonucleotide primers according to claim 6; and (c) visualizing said amplified part of the internal transcribed spacer sequence to determine whether said fungal pathogen is present.

14. The method according to claim 13, wherein said fungal pathogen is selected from the group consisting of *Eutypella vitis, Eutypa lata, Phomopsis viticola* and *Diplodia gossypina*.

15. The method according to claim 13, wherein said organism or diseased organism is a grape plant.

16. The method according to claim 13, wherein the pair of oligonucleotide primers comprises SEQ ID NO: 26 and SEQ ID NO: 27.

17. The method according to claim 13, wherein the pair of oligonucleotide primers comprises SEQ ID NO: 28 and SEQ ID NO: 29.

18. The method according to claim 13, wherein the pair of oligonucleotide primers comprises SEQ ID NO: 28 and SEQ ID NO: 30.

19. The method according to claim 13, wherein the pair of oligonucleotide primers comprises SEQ ID NO: 31 and SEQ ID NO: 32.

20. The method according to claim 13, wherein the pair of oligonucleotide primers comprises SEQ ID NO: 33 and SEQ ID NO: 34.

21. The method according to claim 13, wherein the pair of oligonucleotide primers comprises SEQ ID NO: 35 and SEQ ID NO: 36.

22. A kit comprising a carrier to receive therein one or more containers, at least one of said containers comprising an oligonucleotide primer according to claim 5.

23. A kit comprising a carrier to receive therein one or more containers, at least one of said containers comprising a pair of oligonucleotide primers according to claim 6.

* * * * *